United States Patent [19]
Gil et al.

[11] Patent Number: 5,677,327
[45] Date of Patent: Oct. 14, 1997

[54] METHOD FOR IDENTIFYING MUSCARINIC AGENTS LACKING MIOTIC SIDE EFFECTS

[75] Inventors: Daniel W. Gil, Corona Del Mar; Elizabeth Woldemussie, Laguna Niguel, both of Calif.

[73] Assignee: Allergan, Waco, Tex.

[21] Appl. No.: 493,509

[22] Filed: Jun. 22, 1995

[51] Int. Cl.$^6$ .................................................. A61K 31/415
[52] U.S. Cl. ............................................ 514/397; 514/913
[58] Field of Search .................................... 514/397, 913

[56] References Cited

U.S. PATENT DOCUMENTS 5,264,449  11/1993  Albaugh .................................... 514/397

OTHER PUBLICATIONS

Embase Abstract 93042625, (1993). Olianas et al.
Embase Abstract 93039765, (1993). Schwarz et al.
WPIDS 92–096799 (2), (1992). Mitch et al.

Primary Examiner—Zohreh Fay
Attorney, Agent, or Firm—Robert J. Baran; Martin A. Voet; Howard R. Lambert

[57] ABSTRACT

The present invention provides a method for identifying a compound having muscarinic agonist activity that will lower intraocular pressure without causing miosis which comprises measuring the activity of the compound at the $m_3$ and $m_5$ muscarinic receptors and determining from the activity measurement a compound having at least twice the agonist activity at the $m_5$ receptor as compared to the $m_3$ receptor. Preferably, the method of measuring said muscarinic agonist activity comprises eliciting phosphoinositide hydrolysis in CHO-K1 cells stably expressing the $m_3$ and $m_5$ muscarinic receptor subtypes. The present invention also provides a method of lowering the intraocular pressure in a mammal which comprises administering to said mammal a compound that has been determined to have at least twice the agonist activity at the $m_5$ receptor as compared to the $m_3$ receptor.

2 Claims, No Drawings

METHOD FOR IDENTIFYING MUSCARINIC AGENTS LACKING MIOTIC SIDE EFFECTS

BACKGROUND OF INVENTION

1. Field of the Invention

The present invention is directed to a method for identifying selective muscarinic agents for reducing intraocular pressure without causing miosis and the preparation of pharmaceutical compositions, primarily topically applied ophthalmic compositions, comprising as the active ingredient one or more of said identified compounds. Said identified compounds have the ability to selectively act at the m5 muscarinic receptor as opposed to the m3 muscarinic receptor. Thus, said pharmaceutical compositions are useful for reducing intraocular pressure in animals of the mammalian species without causing the side effect of miosis. In another aspect, the present invention is directed to administering such formulations and compositions to animals of the mammalian species (including humans) for reducing intraocular pressure in the eye.

2. Brief Description of the Art

Glaucoma is an optical neuropathy associated with elevated intraocular pressures which are too high for normal function of the eye, and results in irreversible loss of visual function. It is estimated in medical science that glaucoma afflicts approximately 2 per cent of the population over the age of forty years, and is therefore a serious health problem. Ocular hypertension, i.e. the condition of elevated intraocular pressure, which has not yet caused irreversible damage, is believed to represent the earliest phase of glaucoma. Many therapeutic agents have been devised and discovered in the prior art for the treatment or amelioration of glaucoma and of the condition of increased intraocular pressure which precedes glaucoma.

The drugs currently utilized in the treatment of glaucoma include miotics (e.g., pilocarpine, carbachol, and acetylcholinesterase inhibitors), sympathomimetrics (e.g., epinephrine and dipivalylepinephrine), beta-blockers (e.g., betaxolol, levobunolol and timolol), alpha-2 agonists (e.g., para-amino clonidine) and carbonic anhydrase inhibitors (e.g., acetazolamide, methazolamide and ethoxzolamide). Miotics and sympathomimetics are believed to lower intraocular pressure by increasing the outflow of aqueous humor, while beta-blockers, alpha-2 agonists and carbonic anhydrase inhibitors are believed to lower intraocular pressure by decreasing the formation of aqueous humor. All five types of drugs have potential side effects. Miotics, such as pilocarpine, can cause blurring of vision and other visual side effects which may either decrease patient compliance or require termination of drug therapy. Carbonic anhydrase inhibitors can also cause serious side effects which affect patient compliance and/or necessitate withdrawal of the drug therapy. At least one beta-blocker, timolol, has increasingly become associated with serious pulmonary side effects attributable to its effect on beta-2 receptors in pulmonary tissue.

In particular, many compounds, which lower IOP and therefore are thought to be useful in treating glaucoma, cause side effects such as miosis.

Thus, many ocular hypotensive compounds and agents of the prior art do not provide such treatment or cure for glaucoma and ocular hypertension which is satisfactory in all respects. Therefore, the pharmacological and related arts and sciences continue searching for additional and better anti-glaucoma and ocular hypotensive agents.

SUMMARY OF THE INVENTION

Surprisingly it has been discovered in accordance with the present invention that certain compounds that are effective as anti-glaucoma agents and as agents for reducing intraocular pressure, having the ability to selectively act at the m5 muscarinic receptor, as opposed to the m3 muscarinic receptor, when such agents are applied to the mammalian eye in a pharmaceutical composition, preferably in a topical ophthalmic composition, do not cause miosis. Accordingly, the present invention relates to a method for identifying a compound having muscarinic activity that will lower intraocular pressure without causing miosis which comprises measuring the activity of said compound at the m3 and m5 muscarinic receptors and determining from said activity measurements a compound having at least twice the agonist activity at the m5 receptor as compared to the m3 receptor.

Another aspect of the present invention is a method of treating glaucoma, or ocular hypertension by topically administering to the mammalian eye an ophthalmic composition which contains an amount of a compound to lower intraocular pressure and having selective activity at the m5 muscarinic receptor as opposed to the m3 muscarinic receptor.

The ophthalmic compositions of the invention contain the active ingredient in a concentration range of approximately 0.0001 to 0.1 per cent weight by volume. The composition, itself, includes, in addition to the active ingredient, such excipients which are per se well known in the art for preparing ophthalmic compositions, particularly ophthalmic solutions. Furthermore, in accordance with the method of the invention the ophthalmic compositions, preferably ophthalmic solutions are applied topically to the mammalian eye approximately 1 or 2 times daily.

DETAILED DESCRIPTION OF THE INVENTION

Pharmaceutically acceptable salts of the selective muscarinic agonists can also be used in accordance with the present invention. A pharmaceutically acceptable salts may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, e.g. sodium, potassium, etc. Organic amine salts may be made with amines, particularly ammonium salts such as mono-, di- and trialkyl amines or ethanol amines. Salts may also be formed with caffeine, tromethamine and similar molecules.

For reducing intraocular pressure in a mammalian eye, and particularly for treatment of glaucoma in humans suffering from that condition, the active compounds (or mixtures or salts thereof) are administered in accordance with the present invention to the eye admixed with an ophthalmically acceptable carrier. Any suitable, e.g., conventional, ophthalmically acceptable carrier may be employed. A carrier is ophthalmically acceptable if it has substantially no long term or permanent detrimental effect on the eye to which it is administered. Examples of ophthalmically acceptable carriers include water (distilled or deionized water) saline and other aqueous media. In accordance with the invention, the active compounds are preferably soluble in the carrier which is employed for their administration, so that the active compounds are administered to the eye in the form of a solution. Alternatively, a suspension of the active compound or compounds (or salts thereof) in a suitable carrier may also be employed.

In accordance with the invention the active compounds (or mixtures or salts thereof) are administered in an ophthalmically acceptable carrier in sufficient concentration so as to deliver an effective amount of the active compound or compounds to the eye. Preferably, the ophthalmic, therapeutic solutions contain one or more of the active compounds in a concentration range of approximately 0.0001% to approximately 0.1% (weight by volume) and more preferably approximately 0.0005% to approximately 0.1% (weight by volume).

Preferrably, any method of administering drugs directly to a mammalian eye may be employed to administer, in accordance with the present invention, the active compound or compounds to the eye to be treated. By the term "administering directly" is meant to exclude those general systemic drug administration modes, e.g., injection directly into the patient's blood vessels, oral administration and the like, which result in the compound or compounds being systemically available. The primary effect on the mammal resulting from the direct administering of the active compound or compounds to the mammal's eye is preferably a reduction in intraocular pressure. More preferably, the active useful compound or compounds are applied topically to the eye or are injected directly into the eye. Particularly useful results are obtained when the compound or compounds are applied topically to the eye in an ophthalmic solution (ocular drops).

Topical ophthalmic preparations, for example ocular drops, gels or creams, are preferred because of ease of application, ease of dose delivery, and fewer systemic side effects, such as cardiovascular hypotention. An exemplary topical ophthalmic formulation is shown below in Table I. The abbreviation q.s. means a quantity sufficient to effect the result or to make volume.

TABLE I

| Ingredient | Amount (% W/V) |
| --- | --- |
| Active Compound in accordance with the invention, | about 0.0001 to about 0.1 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |
| Purified Water | as needed to make 100% |

Various preservatives may be used in the ophthalmic preparation described in Table I above. Preferred preservatives include, but are not limited to benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

The ophthalmic solution (ocular drops) maybe administered to the mammalian eye as often as necessary to maintain an acceptable level of intraocular pressure in the eye. In other words, the ophthalmic solution (or other formulation) which contains the selective muscarinic agonist agent as the active ingredient, is administered to the mammalian eye as often as necessary to maintain the beneficial hypotensive effect of the active ingredient in the eye. Those skilled in the art will recognize that the frequency of administration depends on the precise nature of the active ingredient and its concentration in the ophthalmic formulation. Within these guidelines it is contemplated that the ophthalmic formulation of the present invention will be administered to the mammalian eye approximately once or twice daily.

Specific examples of selective muscarinic agonists which are used as the active effective ingredients in the ophthalmic compositions of the present invention may be determined as described and shown below:

METHODS

Chinese hamster ovary (CHO-K1) cells stably expressing the human $m_3$ or $m_5$ receptor subtype were grown to confluency in DMEM/F12 medium containing 10% fetal calf serum and 1 unit/ml penicillin/streptomycin in a 37° C. incubator. Activity of muscarinic agonists in these cells was determined by measuring agonist induced hydrolysis of inositol phospholipids. Confluent cells plated at $0.1 \times 10^6$ cells/well in a 24-well dish were incubated in medium containing 4 μCi/ml myo-[2-$^3$H] inositol overnight. This labels the inositol phospholipids in the cells. The next morning, the cells were washed to remove excess medium and incubated for 10 minutes before and 30 minutes after the addition of various muscarinic agonists in assay buffer containing 10 mM LiCl. The hydrolysis of inositol phospholipids generates inositol phosphates which were extracted and separated on dowex-formate columns and radioactivity determined. Radioactivity of the unhydrolyzed inositol phospholipids was also determined and percent hydrolysis calculated as a measure of agonist activity.

| MAXIMUM RESPONSE BY MUSCARINIC AGONISTS | | |
| --- | --- | --- |
| | CELLS | |
| DRUG | $m_3$ | $m_5$ |
| CARBACHOL | 1 | 1 |
| AGN 190456 | 0.7 ± .07 | 0.84 ± .11 |
| PILOCARPINE | 0.8 ± .09 | 1.1 ± .18 |
| BR-370 | 0.96 ± .4 | 1.1 ± .08 |
| BM-5 | 0.3 ± .03 | 0.3 ± .02 |

Values expressed relative to the maximum response elicited by carbachol

POTENCY OF MUSCARINIC AGONISTS ON
PI HYDROLYSIS IN CRO-K1, m3 AND m5 CELLS
EC 50 (µM)

| DRUG | CELLS | |
|---|---|---|
| | $m_3$ | $m_5$ |
| AGN 190456 | 20 | 5 |
| BM-5 | 0.3 | 0.06 |
| BR-370 | 0.8 | 0.7 |
| PILOCARPINE | 1.5 | 2.0 |
| CARBACHOL | 0.3 | 0.6 |

The $EC_{50}$ was calculated as 50% of the maximum response of the PI hydrolysis
AGN 190456 is 3R, 4R-ethyl-[(1-methyl-1H-imidazol-5-yl) methyl]-2-pyrrolidinone BM-5 is N-Methyl-N-(1-methyl-4-pyrrolidino-2-butynyl)acetamide BM-370 is N-(4-Azetidinyl-2-butynyl)-5-methyl-2-pyrrolidone Of the compounds tested AGN 190456 and BM-5 have a $m_3/m_5$ ratio of 4 and 5, respectively. The remaining compounds have $m_3/m_5$ ratios of from about 0.5 to about 1.1. When the compounds having these lower ratios are tested, IOP-lowering is obtained, but miosis also occurs. When AGN 190456 is tested for lowering IOP, it is effective and elicits minimal miosis. BM-5 is also more potent at the m5 receptor than the m3 receptor, but it is a relatively weak agonist, eliciting only 30% of the hydrolysis elicited by carbachol at the m5 receptor. Thus, it elicits both IOP-lowering and miosis. Thus, in a drug that lower IOP, if it has greater than 30% efficacy at the m5 receptor, the ratio of m3/m5 activity is predictive of the miotic activity of an effective IOP-lowering drug. While not wishing to be bound by theory, it is believed that the m3 and m5 subtypes are located in the iris sphincter and activation of the m5 receptor represses miosis caused by the m3 receptor.

While particular embodiments of the invention have been described, it will be understood, of course, that the invention is not limited thereto since many obvious modifications can be made, and it is intended to include within this invention any such modification as will fall within the scope of the appended claims. For example, the compound for lowering intraocular pressure without causing miosis in a mammal may be administered systemically as well as topically.

In view of the above, it is clear that the scope of the present invention should be interpreted solely on the basis of the following claims, as such claims are read in light of the disclosure.

What is claimed is:

1. A method for identifying a compound having muscarinic activity that will lower intraocular pressure without causing miosis which comprises measuring the activity of said compound at the m3 and m5 muscarinic receptors and determining from said activity measurement a compound having at least twice the agonist activity at the m5 receptor as compared to the m3 receptor and greater than 30% efficacy of carbachol at the m5 receptor.

2. The method of claim 1 wherein said muscarinic agonist activity is measured by determining the ability of a muscarinic agonist to elicit phosphoinositide hydrolysis in CHO-K1 cells stably expressing the m3 and m5 muscarinic receptor subtypes.

\* \* \* \* \*

UNITED STATES PATENT AND TRADEMARK OFFICE
CERTIFICATE OF CORRECTION

PATENT NO. : 5,677,327
DATED : October 14, 1997
INVENTOR(S) : Gil et al

It is certified that error appears in the above-indentified patent and that said Letters Patent is hereby corrected as shown below:

Column 5, line 4; delete "CRO-K1" and insert in place thereof --CHO-K1--

Signed and Sealed this

Twenty-fourth Day of February, 1998

*Attest:*

BRUCE LEHMAN

*Attesting Officer*  *Commissioner of Patents and Trademarks*